United States Patent [19]
Money

[11] 4,399,818
[45] Aug. 23, 1983

[54] DIRECT-COUPLED OUTPUT STAGE FOR RAPID-SIGNAL BIOLOGICAL STIMULATOR

[75] Inventor: David K. Money, Pennant Hills, Australia

[73] Assignee: Telectronics Pty. Ltd., Lane Cove, Australia

[21] Appl. No.: 251,192

[22] Filed: Apr. 6, 1981

[51] Int. Cl.³ .............................................. A61N 1/36
[52] U.S. Cl. ............................................ 128/419 PG
[58] Field of Search ................................ 128/419 PG

[56] References Cited

U.S. PATENT DOCUMENTS

| 4,114,627 | 9/1978 | Lewyn et al. | 128/419 PG |
| 4,114,628 | 9/1978 | Rizk | 128/419 PG |
| 4,300,566 | 11/1981 | Stindt et al. | 128/419 PG |

FOREIGN PATENT DOCUMENTS 2520730 11/1975 Fed. Rep. of Germany ...... 128/419 PG

*Primary Examiner*—William E. Kamm
*Attorney, Agent, or Firm*—Gottlieb, Rackman and Reisman

[57] ABSTRACT

There is disclosed a direct-coupled output stage which is especially advantageous for use in an implantable heart pacer. In order to provide for charge balancing at the electrode/electrolyte interfaces, the electrodes are shorted to each other after a pacing pulse is generated. Not only is the use of a bulky coupling capacitor avoided, but the stored charge dissipates in a much shorter time, thereby minimizing the "blind" interval in the sensing cycle.

27 Claims, 2 Drawing Figures

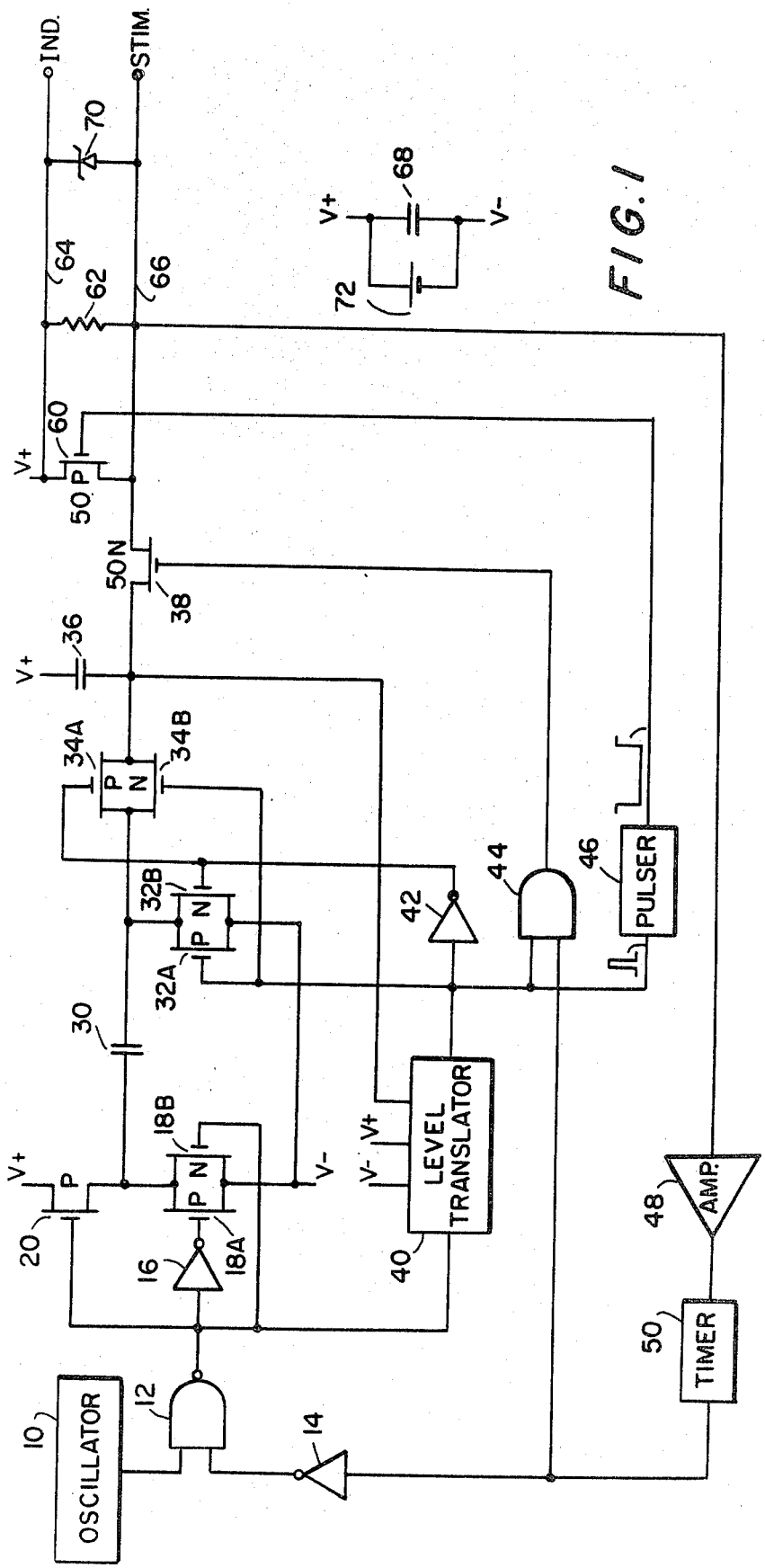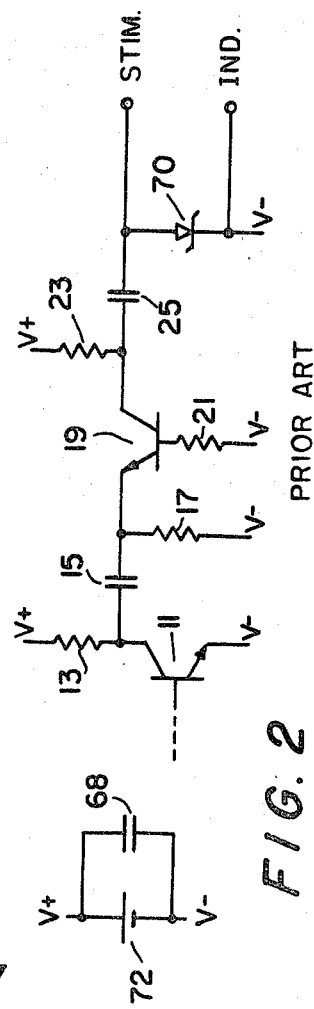
FIG. 1
FIG. 2 PRIOR ART

DIRECT-COUPLED OUTPUT STAGE FOR RAPID-SIGNAL BIOLOGICAL STIMULATOR

This invention relates to output stages for biological stimulators, and more particularly to direct coupled output stages for delivering rapidly-varying signals such as those generated by a heart pacer.

In a typical heart pacer, charge is stored on one or more capacitors. When a pacing pulse is required the charge-storage capacitors are connected in series with the stimulating and indifferent electrode leads, the capacitors discharging through the leads and the electrode/electrolyte interfaces in the patient's tissue. (In general, at least one although not necessarily both electrodes are placed adjacent to heart tissue.) The capacitor which is connected directly to the stimulating electrode lead then recharges through the battery supply and the stimulating electrode. It is a generally accpeted deisgn goal that no net charge be delivered to the heart. Because the average current through a capacitor is zero, the provision of AC coupling insures that there is no net current flow through the stimulating electrode.

There are at least two main disadvantages with the use of AC coupling of this type. First, in addition to the cost of the coupling capacitor, it is bulky and contributes to the size and weight of the pacer. This is not a serious disadvantage in the case of external biological stimulators (heart pacers, or any other type). But the other disadvantage is equally applicable to external biological tissue stimulators. (By an external stimulator is meant a device which is external to the body, but which applies a signal over leads which may be internal.) At least in the case of a heart pacer, the electrode leads are also used to sense electrical activity in the heart. The potential on the stimulating electrode changes abruptly at the start of a pacing pulse, the potential then reverting back slowly as the capacitor connected to the electrode recharges. During this charging process, heart activity signals may be masked. Typically, the potential on the stimulating electrode relative to the (ground) indifferent electrode may be several hundreds of millivolts during the charging cycle, while the electrical activity of the heart may result in a signal of only several millivolts. Filters employed with typical heart pacer sensing circuits are designed to reject the charging current signal, while minimally attenuating signals which reflect heart activity. But there is usually a "blind" period at the start of the sensing cycle, immediately following the generation of a pacing pulse. This period may last 50-100 milliseconds, and can be even longer. The problem is not particularly severe in the case of a single-chamber pacer because heart activity should be ignored by the sensing circuit during the "refractory period" of the heart, which is typically at least as long as the blind period. However, the problem can be much more serious in the case of a dual-chamber pacer where completely independent electrode pairs may not be provided for the two chambers and electrical activity in one heart chamber may have to be detected shortly after a pulse is applied to another chamber; in such a case, rapid charging is important in order to reduce the blind time.

It is to be understood that there are tissue stimulators which are provided with direct-coupled output stages. A bone growth stimulator, for example, applies a direct current to a fracture site where bone growth is to be promoted. Obviously, a DC output stage is mandatory in such a case. The tissue stimulators of concern are those which apply rapidly-varying signals, any signal (AC, pulse, etc.) which varies appreciably (so as to have a biological effect) in less than 10 seconds. A typical stimulator of this type is a heart pacer in which stimulating pulses are generated on the order of every second or so.

It is a general object of my invention to provide a direct-coupled output stage for a rapid-signal biological stimulator, thus avoiding the need for a coupling capacitor and its concomitant disadvantages.

Despite the aforesaid disadvantages of the use of a coupling capacitor, it is almost an anathema in the heart pacer art, for example, to omit the output coupling capacitor. See, e.g., Fisher et al., "Pacemaker Failures Characterized by Continuous Direct Current Leakage", The American Journal of Cardiology, June, 1976. The belief that a coupling capacitor is mandatory is so ingrained in the minds of heart pacer designers that apparently little thought is given even now as to whether the capacitor is actually necessary. However, a careful analysis brings into question not only whether the coupling capacitor is necessary, but whether it even does the job which it is supposed to do.

In any rapid-signal biological stimulator, at least the stimulating electrode is implanted adjacent to the tissue to be stimulated. the indifferent electrode may be implanted nearby, or it may be implanted in tissue far away. But the signal current necessarily flows between the two electrodes. What happens is that an electron flow in the electrode leads is converted to an ion flow at the interfaces with the body electrolyte (body fluids are saline in nature). The equivalent impedance at an electrode/electrolyte interface is not of the same type as that of the body tissue itself between the electrodes, the latter being representable as a discrete resistance. At the interface of each electrode, the impedance is really a distributed RC network—an infinite number of resistors connected in series, with an effective capacitor connected in parallel across each resistor. This is the equivalent circuit through which a pacing current pulse flows, and the distributed capacitance charges. To minimize electrochemical effects there should be no net charge transfer to the tissue. This requires that the stored charge at the electrode/electrolyte interface be recovered. The coupling capacitor, by ensuring that there is no net current flow, theoretically results in total charge recovery.

However, a net current flow of zero through the coupling capacitor, or the electrode leads since they are in series with the capacitor, is not really the important consideration. In theory, charge is stored in the distributed capacitance at each electrode/electrolyte interface, and this charge is recovered after the pacing pulse as the charge storage capacitor is recharged through the battery and a current flows in the opposite direction through the electrode leads. But just because there is no net current through the coupling capacitor does not mean that no ion flow has occurred in the stimulated tissue.

On a purely abstract level, consider the case of a one-second, 10-milliampere current pulse which is delivered through the electrodes. Assume further that current flow in the reverse direction could be actively controlled to have the same duration and magnitude. A symmetrical square-wave current signal would flow through the electrodes, with the average current through the coupling capacitor being zero. When the current flows in one direction, charge is stored on the distributed capacitance at the electrode/electrolyte interfaces. However, this charge does not just "sit" there until it is recovered by a current which flows in the opposite direction. Instead, some of the charge leaks off the distributed capacitance, flows through the body tissue, and is irretrievably "lost". When an identical current pulse is caused to flow in the opposite direction, the remaining charge on the distributed capacitance is recovered. But since some of the original charge has leaked off, the rest of the "recovered" charge must be derived from elsewhere in the tissue. The net current through the coupling capacitor is zero, but there are really two "undesired" ion flows in the tissue—one due to the original leakage, and the other due to the the compensating "recovery" of the charge which was lost. The original leakage is undesirable, but nothing is gained by compounding the problem with an additional ion flow through the tissue. Any damage done by the leakage is not compensated; instead, the compensating ion low only does more damage. The net charge through the coupling capacitor is zero, but the net ion flow, or charge transfer, is not. It is really a case of two wrongs not making a right.

In short, the best possible "charge balance" (minimal net charge transfer) in the tissue is not necessarily reflected by a net current flow of zero through the electrodes.

Consider now another example, one in which a coupling capacitor is not used, i.e., the output stage is direct-coupled to the electrodes, an example which illustrates the principles of the invention. A typical pacing pulse may be 10 milliamperes in magnitude and it may have a duration of 0.5 milliseconds. Suppose that instead of allowing a coupling capacitor to recharge through the electrodes until the current-time product or integral equal 5 milliampere-milliseconds, the electrode leads are shorted to each other instead. Experiments have shown that some 99% of the charge delivered through the electrodes during the pacing pulse is recovered during the first 8 milliseconds following shorting of the electrodes via the leads. This means that the net current flow in the tissue is only about 1% of the peak pulse current.

Where a coupling capacitor is used, the charge recovery is relatively slow because the coupling capacitor is usually returned to the battery supply through a resistor. During the relatively long charge recovery time, e.g., 100 milliseconds, some of the charge on the distributed capacitance is still leaking off, so that this charge can only be "recovered" by an additional ion flow in the tissue toward the end of the charge recovery process. It is the capacitor itself which causes this undesirable ion flow because the only way to achieve a net current flow of zero through the capacitor is for an additional ion flow to take place in order to make up for the charge which has leaked off the distributed capacitance. But if the electrode leads are shorted together, there is a rapid discharge of the distributed capacitance through the short. The discharge is so fast that, as mentioned above, about 99% of the charge is recovered within 8 milliseconds. Although about 1% of the charge has leaked off the distributed capacitance and done its damage, not only is there less leakage because the distributed capacitance discharge is rapid, but the damage is not compounded by causing a totally unnecessary ion flow in the tissue in the opposite direction.

There is no compelling reason for keeping the electrodes shorted for more than 8 milliseconds in this case. Not much more than 99% of the original charge can be recovered; during the first 8 milliseconds, about 1% of the original charge has leaked off and cannot be recovered. The current which flows in the reverse direction falls to a low level by the time 8 milliseconds have expired. There may thus be no reason to keep the electrodes shorted any longer, although it cannot do any harm since shorted electrodes cannot cause unnecessary ion flow (the charge recovery is passive, not active). This means that not only is the use of a costly and bulky coupling capacitor avoided, but the "blind" time is greatly reduced (in the context of a heart pacer); as soon as the shorting circuit, or whatever mechanism is used for coupling the electrodes together and allowing passive charge dissipation, is released, the electrodes can be used for sensing heart activity without the resulting signal being masked by output capacitor recharge current flow (although there still remains an interface voltage component due to the non-recoverable charge).

Of course, the electrodes may be held shorted in this way for even longer than 9 milliseconds, to provide an "automatic" refractory period of desired duration; in a typical ventricular-inhibited (VVI) heart pacer the sensing circuit should not respond to heart activity for perhaps 50 milliseconds or so after a pacing pulse is generated, and the charge recovering shorting circuit is a convenient mechanism for disabling the sensing circuit. In general, I contemplate shorting the electrodes for 0.01–400 milliseconds. Small durations at the lower end of the range may include shorting several times within a burst of narrow pulses or intermittently following a pulse, allowing sensing in between. Especially in the case of a heart pacer, a shorting interval of 8–50 milliseconds is preferred.

The invention is particularly advantageous for use in implantable devices in which the elimination of any component, especially a bulky capacitor, is desirable. It should also be appreciated that the invention is highly advantageous in the case of a typical heart pacer which is provided with only a single potential source. Were two sources of opposite polarities provided, it might be thought that the use of a coupling capacitor could be avoided by switching the two potential sources to the stimulating electrode; one source would be used for controlling the application of a pulse to the stimulating electrode, and the other would then be used to control active discharge of the distributed capacitance. But conventional heart pacers are not provided with two sources; only a single-polarity source is used, and a coupling capacitor has been believed to be necessary for charge balancing purposes. It is in fact not needed, or even desirable, for the reasons described above.

All of this does not imply that the use of capacitors can be avoided. In fact, in the illustrative embodiment of my invention, a heart pacer, two large capacitors are used. One capacitor, typically 5–15 uF, is connected across the battery in the pacer in order to stabilize the potential busses. This capacitor has nothing to do with the delivery of pacing pulses or charge recovery, and is used only so that transients resulting from the pacing pulses do not affect the powering of the other circuits in the pacer. A second capacitor, typically 15 uF, is used for storing charge to be delivered during the application of a pacing pulse. An ordinary battery used in a heart pacer cannot supply the relatively large current which is required for a pacing pulse. The conventional technique for deriving this relatively large current is to charge a storage capacitor from the battery, and to rapidly discharge the capacitor into the electrode leads whenever a pacing pulse is required. I also utilize such a capacitor, but it is not a coupling capacitor because although it delivers a pacing pulse directly to the stimulating electrode, charge is not recovered through it at the termination of the pulse. The capacitor does not recharge through the electrodes between pacing pulses. Rather, the capacitor charges once again in preparation for another pacing pulse through a circuit in the pacer which does not involve a flow of current through the electrode leads. Charge balance is achieved by shorting the two electrodes to each other. The storage capacitor does not function as a coupling capacitor because all currents which flow through the stimulating leads do not flow through it.

A conventional prior art heart pacer often includes a "voltage doubling" circuit. Such a circuit involves the use of two large storage capacitors (in addition to the third filter capacitor across the battery). The two capacitors are charged separately to the potential of the battery, one of the capacitors being a coupling capacitor and thus being charged through the electrode leads for reasons of charge balance. When a pacing pulse is required, and if a pulse of double magnitude is desired, the two capacitors are connected in series with the electrode leads. In the illustrative embodiment of my invention, I also provide for voltage doubling. However, instead of using two large 30 uF storage capacitors, I utilize only one 15 $\mu$F component, together with a small, typically 0.1 uF, "pump" capacitor which controls a potential across the storage capacitor which is equal to twice the battery supply. Thus the net result is that one large capacitor may be omitted and the other reduced to half size. But even were two large capacitors used to achieve voltage-doubling, by not using either of them for controlling charge balance undesirable ion flow in the body tissue is avoided. In other words, it is better from a physiological point of view to provide direct coupling even if there is no net reduction in components, not to mention that the use of DC coupling allows the blind time to be reduced considerably.

In one experiment which was conducted, the electrodes were placed in a 9 gram/liter saline solution to simulate the body tissue. Half-millisecond, 10-milliampere pulses were generated at a repetition rate of 1 per second, and the net current in the leads was measured for different shorting intervals following the application of each pulse. The following table depicts the net current, i.e., charge imbalance, for different shorting intervals:

| Shorting Interval | Net Current |
|---|---|
| 1 msec | 1.40 $\mu$A |
| 1.75 msec | 0.62 $\mu$A |
| 2 msec | 0.44 $\mu$A |
| 2.75 msec | 0.15 $\mu$A |
| 3.2 msec | 0.13 $\mu$A |
| 5 msec | 0.07 $\mu$A |
| 8 msec | 0.04 $\mu$A |

Further objects, features and advantages of the invention will become apparent upon consideration of the following detailed description in conjunction with the drawing, in which:

FIG. 1 depicts the illustrative embodiment of the invention; and

FIG. 2 depicts a portion of a typical prior art AC-coupled pacer output stage.

The prior art pacer output stage of FIG. 2 includes a 3-volt potential source 72 with a filter capacitor 68 connected across it. The two voltage busses for powering the pacer circuit are labelled V+ and V−. Capacitor 68 is typically 5–15 $\mu$F in magnitude, and its use is necessary, as described above, for reasons other than pacing pulse delivery or charge balance.

The remainder of the circuit shown in FIG. 2 is the output stage itself; the circuits for sensing heart activity and timing pacing pulses are not shown. Between pacing pulses, both of transistors 11 and 19 are held off. Capacitor 15 charges between the two potential busses, through resistors 13 and 17, with the right side of the capacitor being negative relative to the left side well before there is a need to generate another pacing pulse. At the same time, capacitor 25 is also actively charged through resistor 23, the stimulating and indifferent electrode leads, the two electrodes, and the heart tissue. It is during this interval that charge is recovered from the distributed capacitance at the electrode/electrolyte interfaces, with the right side of capacitor 25 charging to a negative potential relative to the left side. Zener diode 70 is the conventional protective diode for preventing an excessive potential from appearing across the two electrodes, and need not be considered further herein. When a pacing pulse is to be delivered, a positive pulse is applied to the base of transistor 11. The transistor turns on and shorts the left side of capacitor 15 through it to the negative voltage bus. The negative potential step is extended through capacitor 15 to the emitter of transistor 19, so that this transistor turns on as well. Capacitors 15 and 25 are now connected in series between the indifferent and stimulating electrodes, and a negative pulse is applied to the stimulating electrode to pace the heart.

At the termination of the pulse, transistor 11 is turned off, and with it transistor 19 turns off as well. Capacitor 15 now recharges through resistors 13 and 17, and capacitor 25 recharges through resistor 23 and the heart tissue. (Resistor 23 is typically 15K in magnitude; it should not be too much larger or else it will take too long for capacitor 25 to charge.) This technique of charging each of the capacitors to the full supply potential, and then connecting them in series when a pacing pulse is to be delivered, results in a pulse amplitude which is twice the amplitude of the battery. Each of capacitors 15 and 25 has a magnitude of 30 uF, the two capacitors thus having an equivalent capacitance of 15 uF when they are connected in series to deliver a pacing pulse.

Capacitor 25 serves two functions. First, it is one of the two storge capacitors utilized to achieve voltage doubling and to store sufficient charge for a large current pulse. Second, capacitor 25 serves as an AC coupling capacitor. Since the net current through the capacitor must be zero, the net current flow through the electrodes is necessarily zero. As described above, however, despite the fact that a coupling capacitor has been thought to be necessary, it does not result in charge balance. In fact, while perfect charge balance is not possible due to leakage from the distributed capacitance at each electrode/electrolyte interface, capacitor 25 actually causes an unnecessary ion flow at the electrode/electrolyte interfaces. By controlling a net current flow of zero, there is a larger net transfer of charge than would otherwise result.

It might be thought that capacitor 25 is needed for another reason, namely, to prevent the application of a continuous DC potential to the stimulating electrode should the switching transistors in the pacer fail. However, especially in the case of an integrated circuit pacer, the switches are usually more reliable than the capacitor.

The pacer of FIG. 1 is shown more complete than the prior art pacer of FIG. 2; all of the components necessary for an operative pacer are depicted, although some of these components are shown in block-diagram form only since they are well known to those skilled in the art. The stimulating and indifferent electrodes are connected to respective leads 66,64, with the same Zener diode 70 being placed across them. Unlike resistor 23 in FIG. 1, resistor 62 is a high-impedance component, typically 100K, since it is not used for recharging a storage capacitor. Capacitor 68 in FIG. 1 serves the same function as capacitor 68 in FIG. 2; it is a filter capacitor for the 3-volt power supply. Capacitor 36 in FIG. 2 is the storage capacitor which causes a pacer pulse to be delivered when it discharges. All of the charge delivered to the stimulating electrode is derived from this capacitor. Thus while two 30-uF capacitors 15 and 25 are utilized in the prior art circuit of FIG. 2 and provide an equivalent series capacitance of 15 uF, capacitor 36 need have a value of only 15 uF. This capacitor, which is charged to twice the battery potential as will be explained below, delivers the same shape stimulating current pulse as do the two 30-uF capacitors in the circuit of FIG. 2. Capacitor 30 in FIG. 1 is a very small "pump" capacitor of 0.1 uF magnitude. As will be described, this capacitor is used to pump up capacitor 36 to a potential which is equal to twice that of the supply.

Amplifier 48 is a conventional sense amplifier which responds to electrical activity in the heart; it detects a natural heartbeat. The output of timer 50 is normally low. The pacer functions on "demand" (VVI mode) in that a pacing pulse is generated only when it is required. If timer 50 is adjusted to provide a pacing rate of 60 beats per minute, the output of the timer will remain low for as long as natural heartbeats are detected at least once every second. But whenever one second expires without a natural heartbeat having occurred, the output of timer 50 goes high for 0.5 milliseconds. This results in the generation of a pacing pulse.

As long as the heart is beatng normally and the output of timer 50 is low, the output of inverter 14 is high in order to enable one input of NAND gate 12. The other input of the gate is connected to the output of 1-kHz oscillator 10. Thus the output of gate 12 is alternately pulsed high and low at a 1-kHz rate. When the gate output is low, transistor 20 is held on, and transistors 18A,18B are held off. These two latter transistors comprise a conventional transmission gate, with inverter 16 controlling the application of opposite potential levels to the gate terminals. The output of gate 12 is also connected to the input of level translator 40. This conventional device functions to provide a low potential at its output when its input (the output of gate 12) is low. Thus when transistor 20 is on and transistors 18A,18B are off, the level translator and inverter 42 cause transistors 32A,32B to stay on and transistors 34A,34B to stay off. Thus current flows from the positive supply bus through transistor 20, capacitor 30 and transistors 32A,32B to the negative bus, with capacitor 30 charging and its left side becoming positive relative to its right side.

The only reason for providing level translator 40 is that in order to fully turn off N-channel transistor 34B, its gate should be held at the most negative potential in the circuit. The most negative potential is not necessarily the potential of the V-bus because capacitor 36 charges to twice the battery supply and thus the bottom side of the capacitor goes even more negative than the V-potential on the negative bus. For this reason, the potential at the bottom side of capacitor 36 is extended to level translator 40; the level translator output, when the output of NAND gate 12 is low, is always the most negative of its two negative potential inputs—either the V-potential or the potential at the bottom side of capacitor 36. When the output of NAND gate 12 is high, the output of level translator 40 is equal to the potential of the V+ bus.

The outputs of the level translator and inverter 42 hold the transmission gate comprising devices 34A,34B off when the transmission gate comprising devices 32A,32B is on. Thus during the charging of capacitor 30, capacitor 30 is not coupled to capacitor 36.

During alternate half cycles of the oscillator operation, the output of gate 12 is high. The high potential applied to the gate of device 20 holds it off. At this time devices 32A,32B are also off, and it is now devices 18A,18B,34A and 34B which conduct. Consequently, there is a series connection between the V+ and V− busses which consists of capacitors 30 and 36, and two transmission gates. Charge on capacitor 30 is transferred to capacitor 36, and the voltage across the latter is increased. The build-up is in steps. During alternate half cycles of operation capacitor 30 is charged. Between these cycles, charge on capacitor 30 is transferred to capacitor 36. Because capacitor 30 is always charged with its leftmost end being positive relative to its rightmost end, each time that charge is delivered to capacitor 36 its bottom end goes negative relative to its top end. The voltage changes across capacitor 36 get smaller and smaller as capacitor 36 charges, but in considerably less than one second capacitor 36 becomes charged to twice the battery supply.

When the sense amplifier circuit determines that a pacing pulse is required, the output of timer 50 goes high for 0.5 milliseconds. The output of inverter 14 goes low, and the output of gate 12 goes high. This in turn causes the output of level translator 40 to go high to enable one input of gate 44. The other input of the gate is connected directly to the output of timer 50, so the output of gate 44 goes high for 0.5 milliseconds. Since the output of the gate is connected to the gate of transistor 38, this transistor conducts and the charge on storage capacitor 36 is delivered through the device to the stimulating electrode, current flowing through the heart tissue and the indifferent electrode to the V+ supply. The duration of the pulse, during which time capacitor 36 discharges, is 0.5 milliseconds since that is for how long the output of gate 44 remains high. It should be noted that transistor 38 is a 50 N device, meaning that its "on" resistance is 50 times less than the "on" resistances of the other transistors thus far considered. A very low resistance in the electrode leads is desired when a stimulating pulse is to be delivered to the patient's heart, and it is for this reason that transistor 38 is a "large" device.

During the time that a pacing pulse is being delivered, the output of gate 12 is high. Thus capacitor 36 is not only connected through transistor 38 to the stimulating electrode lead, but also through transmission gate 34A,34B, capacitor 30, and transmission gate 18A,18B to the negative supply bus. This is of no moment, however, since negligible current is diverted from the stimulating electrode lead to capacitor 30 due to the relative small size of capacitor 30.

Pulser 46 is triggered at the trailing edge of the 0.5-millisecond positive pulse applied to its input. When the pulser is triggered, it generates a negative pulse whose duration controls for how long electrode leads 64,66 are shorted to each other so that the charge stored on the distributed capacitance at the electrode-electrolyte interfaces can be recovered. The output of the pulser is applied to the gate of transistor 60, and when the pulser output goes low this device turns on. Transistor 60 is also large in size; it has a very low "on" impedance so that the fastest possible discharge or recovery of the distributed capacitance takes place through the shorted electrode leads. As soon as the pulser output goes high once again, transistor 60 turns off. The duration of the shorting of the electrode leads is independent of the recharging of capacitor 36. At the end of the 0.5-millisecond pacing pulse, the output of gate 44 goes low so that transistor 38 is turned off. This isolates the two electrode leads from the remainder of the circuit which immediately begins to pump up capacitor 36 in preparation for another pacing pulse.

It should be noted that while the two electrode leads are shorted together, sense amplifier 48 is disabled. Although not shown, it is to be understood that this amplifier responds to the differences in the potentials of the stimulating and indifferent leads, and while they are both shorted together sensing is disabled. In a conventional demand pacer, an absolute refractory period of about 100 milliseconds is desired; the sensing amplifier should not "detect" heart activity which results from the stimulating pulse itself, nor should that stimulating pulse be detected and interpreted as a natural heartbeat. Refractory-period control is "automatic" in that no additional circuit must be provided to disable the sense amplifier while the leads are shorted to each other. For a conventional VVI pacer, the duration of the pulse at the output of pulser 46 could be adjusted to be as high as 300 milliseconds. In other cases where a short refractory period is desired, the pulse should be shorter. As discussed above, a pulse as short as 8 milliseconds still results in practically total charge recovery.

The importance of a low "on" impedance for transistor 60 should be appreciated. Even if the transistor is held on for 300 milliseconds, what is desired is rapid charge recovery. As mentioned above, one of the problems with prior art pacer circuits is that during the actual charge recovery there is leakage from the distributed capacitance and the charge which leaks away cannot possibly be recovered. Prior art circuits needlessly cause a reverse ion flow which really serves no purpose other than to control a net current of zero through the electrodes, and this serves no useful purpose in and of itself. In the circuit of FIG. 1, although any charge which does not leak off the distributed capacitance at the electrode/electrolyte interfaces does not result in a needless compensating reverse ion flow since the charge balancing process is passive (shorting of the electrodes) rather than active, it is still desirable to minimize charge leakage. For this reason, the most effective shorting of the electrode leads is desirable, and this is accomplished by providing a very low "on" impedance for device 60.

Both of switches 38 and 60 should have "on" impedances of under 200 ohms. The switches, as well as the capacitor pump, are further described in my copending application Ser. No. 251,191, filed on even date herewith and entitled Voltage Multiplier For Implantable Tissue Stimulator, which application is hereby incorporated by reference.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What I claim is:

1. A heart pacer comprising a battery supply, a pair of electrodes for applying a stimulating pulse to the heart of a patient, means connected to at least one of said electrodes for sensing heart activity, storage capacitor means, means responsive to said sensing means for determining the need for a stimulating pulse and in response thereto for connecting said storage capacitor means across said electrodes to apply a stimulating pulse to said patient's heart, means for charging said storage capacitor means from said battery supply following the application of a stimulating pulse to said patient's heart, and means operative following the application of a stimulating pulse to said patient's heart for coupling said electrodes directly to each other and independent of said battery supply to allow charge stored in the interfaces between said electrodes and said patient's tissue as a result of said stimulating pulse to be largely recovered, through said electrodes.

2. A heart pacer in accordance with claim 1 wherein said coupling means is operated for a time duration in the range 0.01–400 milliseconds.

3. A heart pacer in accordance with claim 2 wherein said connecting means disconnects said storage capacitor means from said electrodes simultaneously with the operation of said coupling means so that said storage capacitor means can be charged from said battery supply while the charge stored in said patient's heart is recovered through said electrodes.

4. A heart pacer in accordance with claim 2 wherein said coupling means shorts said electrodes to each other.

5. A heart pacer comprising electrode means for supplying a stimulating current to the heart of a patient, means for sensing heart activity, control means responsive to said sensing means for determining the need for a stimulating current and in response thereto for causing a stimulating current to flow through said electrode means, and means operative following operation of said control means for enabling a passive discharge of the distributed capacitance in said patient's heart.

6. A heart pacer in accordance with claim 5 wherein said enabling means is operated for a time duration in the range 0.01–400 milliseconds.

7. A heart pacer in accordance with claim 5 wherein said electrode means consists of two electrodes, and said enabling means is operative to short said two electrodes to each other.

8. A heart pacer in accordance with claim 5 wherein the pacer is powered from a single source of potential, and said control means is operative to cause current flow through said electrode means in only one direction.

9. A heart pacer in accordance with claim 5 wherein said sensing means is connected to said electrode means and is disabled from sensing heart activity while said enabling means is operated.

10. A heart pacer in accordance with claim 9 wherein said enabling means is operated for a time duration in the range 0.01–400 milliseconds.

11. A heart pacer in accordance with claim 10 wherein said electrode means consists of two electrodes, and said enabling means is operative to short said two electrodes to each other.

12. A heart pacer in accordance with claim 11 wherein the pacer is powered from a single source of potential, and said control means is operative to cause current flow through said electrode means in only one direction.

13. A biological tissue stimulator for applying a rapidly varying signal to a site which is to have minimal net charge transfer comprising electrode means for applying a stimulating current to said site, control means for causing a rapidly varying direct-coupled stimulating current to flow through said electrode means, and means operative following operation of said control means for enabling a passive discharge of the distributed capacitance at said site.

14. A biological tissue stimulator in accordance with claim 13 wherein said enabling means is operated for a time duration in the range 0.01–400 milliseconds.

15. A biological tissue stimulator in accordance with claim 13 wherein said electrode means consists of two electrodes, and said enabling means is operative to short said two electrodes to each other.

16. A biological tissue stimulator in accordance with claim 13 wherein the stimulator is powered from a single source of potential, and said control means is operative to cause current flow through said electrode means in only one direction.

17. A biological tissue stimulator in accordance with claim 13 wherein said control means is disabled from operating while said enabling means is operated.

18. A biological tissue stimulator in accordance with claim 17 wherein said enabling means is operated for a time duration in the range 0.01–400 milliseconds.

19. A biological tissue stimulator in accordance with claim 18 wherein said electrode means consists of two electrodes, and said enabling means is operative to short said two electrodes to each other.

20. A biological tissue stimulator in accordance with claim 19 wherein the stimulator is powered from a single source or potential, and said control means is operative to cause current flow through said electrode means in only one direction.

21. An output circuit for a biological tissue stimulator to stimulate a site for which low net charge transfer is desired comprising a pair of electrodes for causing current flow through said site, charge storing means, means for connecting said charge storing means in series with said pair of electrodes when a stimulating current is to be delivered, and means for coupling said pair of electrodes to each other following operation of said connecting means.

22. An output circuit in accordance with claim 21 wherein said connecting means is connected between said charge storing means and one of said electrodes, and said coupling means couples the other of said electrodes to the junction of said connecting means and said one electrode.

23. An output circuit in accordance with claim 22 wherein said coupling means is operated for a time duration in the range 0.01–400 milliseconds.

24. An output circuit in accordance with claim 23 wherein the stimulator is powered from a single source of potential, and said charge storing means is connected to said electrodes only when current flows through said electrodes in one direction.

25. An output circuit in accordance with claim 22 wherein the stimulator is powered from a single source of potential, and said charge storing means is connected to said electrodes only when current flows through said electrodes in one direction.

26. An output circuit in accordance with claim 21 wherein said coupling means is operated for a time duration in the range 0.01–400 milliseconds.

27. An output circuit in accordance with claim 21 wherein the stimulator is powered from a single source of potential, and said charge storing means is connected to said electrodes only when current flows through said electrodes in one direction.

* * * * *